United States Patent [19]

Bhattacharya

[11] Patent Number: 4,879,266
[45] Date of Patent: Nov. 7, 1989

[54] CATALYST FOR PREPARATION OF DIMETHYL CARBONATE

[75] Inventor: Ajit K. Bhattacharya, Hopewell Junction, N.Y.

[73] Assignee: Texaco Inc., White Plains, N.Y.

[21] Appl. No.: 218,766

[22] Filed: Jul. 14, 1988

Related U.S. Application Data

[62] Division of Ser. No. 652,246, Sep. 20, 1984, Pat. No. 4,785,130.

[51] Int. Cl.$^4$ .............................................. B01J 31/02
[52] U.S. Cl. ................................... 502/164; 502/165; 502/169; 502/171
[58] Field of Search ................ 502/164, 165, 169, 171

[56] References Cited

U.S. PATENT DOCUMENTS

| | | | |
|---|---|---|---|
| 3,952,045 | 4/1976 | Gaenzler et al. | 260/463 |
| 4,113,762 | 9/1978 | Gaenzler et al. | 558/277 |
| 4,625,044 | 11/1986 | Curnutt | 558/277 |
| 4,642,374 | 2/1987 | Lucy et al. | 502/165 X |

FOREIGN PATENT DOCUMENTS 7604857 11/1976 Netherlands ........................ 260/463

OTHER PUBLICATIONS

Itatani et al., *Chem. Ab.*, vol. 91 (1979), p. 74204v.
Saegusa et al., *J. Org. Chem.*, vol. 35 (1970), pp. 2976–2978.
Romano et al., *Ind. Eng. Chem. Prod. Res. Dev.* (1980), vol. 19, pp. 396–403.

*Primary Examiner*—Patrick P. Garvin
*Attorney, Agent, or Firm*—Robert A. Kulason; James J. O'Loughlin; Carl G. Seutter

[57] ABSTRACT

An organic carbonate such as dimethyl carbonate is prepared by reacting an alcohol such as methanol, oxygen, and carbon monoxide in the presence of a catalyst system containing Cu(OMe)Cl as catalyst and boron trifluoride, calcium chloride, benzyltriethylammonium chloride, etc. as promoters.

11 Claims, No Drawings

CATALYST FOR PREPARATION OF DIMETHYL CARBONATE

This is a division, of application Ser. No. 06/652,246, filed Sept. 20, 1984 and now Pat. No. 4,785,130.

FIELD OF THE INVENTION

This invention relates to the preparation of diorganocarbonates. More particularly it relates to the preparation of dimethyl carbonate.

BACKGROUND OF THE INVENTION

Diorganocarbonates, typically dimethyl carbonate, may be prepared by the oxidative carbonylation of alcohols in the presence of a catalyst. Typically methanol is reacted with carbon monoxide and oxygen to prepare dimethyl carbonate. The reaction is carried out in the presence of a catalyst; and those skilled in the art constantly seek new catalysts to lower costs, and to improve reaction conditions, yield, rate of production, etc.

There is a substantial body of prior art relating to the production of organic carbonates. Illustrative of these references are the following:

U.S. Pat. No. 3,114,762 to Mador et al discloses as catalysts metal salts including chlorides and bromides of platinum and palladium plus an oxidizing agent such as iron or copper salts having the same anion.

U.S. Pat. No. 3,227,740 to Fenton discloses as catalyst mercuric halides or carboxylates.

Saegusa et al, *J. Org Chem.*, 35, 2976–2978 (1970) discloses the reaction of CO with copper alkoxides including the dimethoxide, the di-allyloxide, the chloride methoxide, and the acetylacetonate methoxide.

Romano et al IEC Prod. Res. Dev. 19, 396–403 (1980) discloses as catalyst cuprous chloride/cupric chloride methoxide.

U.S. Pat. No. 4,218,391 to Romano et al discloses as catalysts salts of metals of Group IB, IIB, and VIII, preferably monovalent copper such as cuprous bromide, chloride, or perchlorate.

U.S. Pat. No. 4,318,862 to Romano et al discloses as catalyst salts of metals of Groups IB, IIB, or VIII, typically a copper salt such as CuCl.

U.S. Pat. No. 3,846,468 to Perrotti et al discloses as catalysts cuprous chloride complexes with an organic ligand such as pyridine, dipyridyl, imidazole, phenanthroline, alkyl or aryl phosphines, dimethyl sulfoxide, dimethyl formamide, quinuclidine, acetonitrile, benzonitrile, malonitrile, succinodinitrile, or adiponitrile.

U.S. Pat. No. 3,980,690 to Cipriani et al discloses as catalyst a complex of copper chloride and poly-4-vinylpyridine.

Rivetti et al, *J. Organometallic Chem*, 174 (1979) 221–226 discloses as catalysts palladium(II) complexes in the presence of ligands and added bases. Alkyl phosphines are said to inhibit carbonylation almost completely. The presence of tertiary amines enhances the formation of dimethyl carbonate. Low yields (6% or less) of dimethyl carbonate are obtained with $Pd(OAc)_2$ in the presence of ligands such as $R_3P$ where R is $PC_6H_4OCH_3$. Yield is increased to 61% in the presence of base such as diisopropylethylamine.

U.S. Pat. No. 3,952,045 to Gaenzler et al discloses as catalysts organic phosphorus compounds such as phosphine oxide, phosphite, phosphate, or phosphonate plus copper halides.

U.S. Pat. No. 4,360,477 to Hallgren et al discloses as catalysts cupric halides inter alia.

Yang et al CA 86, 171868u (1977) discloses as catalysts $PdCl_2$, $CuCl_2$, $MnCl_2$, and LiCl.

Lapidus et al CA 93, 72328j (1980) discloses as catalysts $MnCl_2$, $KMnO_4$, $CuCl_2$, LiCl, and $Mn(OAc)_3$.

Itatani, Japanese patent publication 54-24827 pub 24 Feb. 1979 discloses as catalysts cuprous halides plus as auxiliary catalyst a halide of an alkali metal or an alkaline earth metal.

U.S. Pat. No. 4,370,275 to Stammann et al discloses as catalysts compositions containing copper, chemically bonded oxygen, and halogen and a nitrogen base. A typical catalyst contains CuO or $Cu(OCl)_2$ and n-butylamine inter alia. Preferred combinations include: $CuCO_3$, $Cu(OH)_2$; $CuCl_2$ and pyridine hydrochloride etc.

U.S. Pat. No. 4,131,521 to Cipris et al discloses an electrochemical process utilizing a non-fluoride halide-containing electrolyte.

U.S. Pat. No. 4,113,762 to Gaenzler et al discloses as catalysts complexes of copper (as CuCl) with $VCl_3$, $CrCl_3$, $FeCl_3$, $CoCl_2$, $AlCl_3$ or $SiCl_4$.

U.S. Pat. No. 4,361,519 to Hallgren discloses as catalysts (i) Bronsted bases such as a quaternary ammonium, phosphonium, or sulfonium compound or an alkoxide or hydroxide of alkali metal or alkaline earth metal or a salt of a strong base and a weak acid or amines etc. plus (ii) a Group VIIIB element Ru, Rh, Pd, Os, Ir, or Pt plus (iii) oxygen plus (IV) a redox catalyst such as a Mn or Co containing catalyst. A typical system includes (i) a pentamethylpiperidine, (ii) $PdBr_2$ and (iii) pyridine adduct of salicylaldehyde-ethylene diamine Co(II) complex.

European Pat. No. 0,071,286 to Drent discloses as catalysts copper compounds such as halide (in the presence of an amine) plus a sulfone such as dimethyl sulfone or a sulfolane.

It is an object of this invention to provide a method for preparation of dimethyl carbonate. Other objects will be apparent to those skilled in the art.

STATEMENT OF THE INVENTION

In accordance with certain of its aspects, this invention is directed to a method of preparing a carbonic acid ester $(RO)_2CO$ wherein R is a hydrocarbon group selected from the group consisting of alkyl, alkaryl, aralkyl, cycloalkyl, and aryl hydrocarbon groups which comprises reacting an alcohol ROH with carbon monoxide in the presence of a catalyst system containing:

(a) as catalyst a copper hydrocarbonoxy halide Cu(OR')X wherein R' is a hydrocarbon group selected from the groups consisting of alkyl, alkaryl, aralkyl, cycloalkyl, and aryl and X is halide; and (b) as promoter MX, $BX_3$, $BR'_3$, $B(OR')_3$, $R'R_3PX$, or $R'NR_3X$ wherein M is a metal of Group I, IIA, IIB, IIIA, IIIB, IVB or VIII thereby forming product carbonic acid ester; and recovering said product carbonic acid ester.

In accordance with certain of its other aspects, this invention is directed to a novel catalyst system containing.

(a) as catalyst a copper hydrocarbonoxy halide Cu(OR')X wherein R' is a hydrocarbon group selected from the group consisting of alkyl, alkaryl, aralkyl, cycloalkyl, and aryl and X is halide; and (b) as promoter MX, $BX_3$, $BR'_3$, $B(OR')_3$, $R'R_3PX$, or $R'NR_3X$ wherein M is a metal of Group I, IIA, IIB, IIIA, IIIB, IVB or VIII thereby forming product carbonic acid ester; and recovering said product carbonic acid ester.

The charge alcohol which may be employed in practice of the method of this invention may include those characterized by the formula ROH.

In the above compound, R may be a hydrocarbon group selected from the group consisting of alkyl, aralkyl, cycloalkyl, aryl, and alkaryl, including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, beta-phenylethyl, etc. When R is cycloalkyl, it may typically be cylohexyl, cycloheptyl, cyclooctyl, 2-methylcycloheptyl, 3-butylcyclohexyl, 3-methylcyclohexyl, etc. When R is aryl, it may typically be phenyl, naphthyl, etc. When R is alkaryl, it may typically be tolyl, xylyl, etc. R may be inertly substituted i.e. it may bear a non-reactive substituent such as alkyl, aryl, cycloalkyl, ether, etc. Typically inertly substituted R groups may include 2-ethoxyethyl, carboethoxymethyl, 4-methyl cyclohexyl, etc. The preferred R groups may be lower alkyl, i.e. $C_1-C_{10}$ alkyl, groups including eg methyl, ethyl, n-propyl, i-propyl, butyls, amyls, hexyls, octyls, decyls, etc. R may preferably be methyl.

The charge alcohol may be a phenol i.e. when R is aryl. The notation ROH is intended to include polyols such as ethylene glycol, glycerine, sorbitol, poly(oxyalkylene) polyols, etc; in these latter compounds, the formula may more typically be represented as $R(OH)_n$ wherein R is derived from an alkyl group and n is an integer, typically 2-10.

Typical charge alcohols which may be employed include:

TABLE I methanol
ethanol
n-propanol
i-propanol
benzyl alcohol
phenol
ethylene glycol
glycerine
sorbitol
poly (oxyethylene-10) glycol etc.

Preferred are the lower ($C_1-C_3$) alkanols; and most preferred is methanol.

The carbon monoxide charge which may be employed may be a pure gas. More commonly it may be a synthesis gas of high purity from which most of the hydrogen and carbon dioxide have been removed.

The catalyst system of this invention may contain
(a) as catalyst a copper hydrocarbonoxy halide Cu-(OR')X wherein R' is a hydrocarbon group selected from the group consisting of alkyl, alkaryl, aralkyl, cycloalkyl, and aryl and X is halide; and
(b) as promoter $MX_n$, $BX_3$, $BR'_3$, $B(OR')_3$, $R'R_3PX$, or $R'NR_3X$ wherein M is a metal of valence n of Group I, IIA, IIB, IIIA, IIIB, IVB, or VIII thereby forming product carbonic acid ester; and
recovering said product carbonic acid ester.

In the copper hydrocarbonoxy halide Cu(OR')X, X is fluorine, chlorine, bromine, or iodine. Preferably X is chlorine or bromine and more preferably chlorine.

R' may be selected from the same group as R; and preferably R' is lower alkyl i.e. $C_1-C_{10}$ alkyl. Preferably R' is methyl. Typical compounds may include:

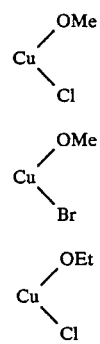

The promoter may be $BX_3$, $BR'_3$, or $B(OR')_3$. It may for example be $BF_3$ as a $BF_3$-etherate, preferably with diethyl ether i.e. $BF_3(C_2H_5)_2O$. Other etherates with dimethyl ether, di-n-propyl ether, tetrahydrofuran, dioxane, etc. may be employed. $BF_3$ without any ether is more preferred. The promoter may be $BR_3$ typified by triphenyl boron or $B(OR)_3$ typified by $B(OCH_3)_3$.

The promoter may be $MX_n$ wherein n is the valence of M. M is a metal of Group IA (Li, K, etc), Group IIA (Be, Mg, Ca, Sr, Ba), Group IIB (Zn, Cd, Hg), Group IIIA (B, Al, etc), Group IIIB (Sc, Y, La etc), Group IVB (Ti, Zr, etc), or Group VIII (Fe, Co, Ni, Ru, Rh, Pd, Os, Ir, Pt). When the metal is a Group VIII metal, it is preferably other than Fe, Co, or Ni. The preferred metals are those of Group IIA, preferably magnesium Mg or calcium Ca. The preferred $MX_n$ may be $CaCl_2$. It should be noted that although M may be sodium, the results attained in terms of yield are much less satisfactory than attained eg, with calcium. When M is potassium, the initial yield is also low, but it increases if the catalyst and promoter are recycled. Others which may be employed include LiCl, $MgCl_2$, KCl, $PdCl_2$, etc.

The promoter may be a quaternary phosphonium salt $R''R_3PX$ typified by the following:

TABLE III $(C_6H_5CH_2)P(C_6H_5)_3Cl$
$(C_4H_9)_4PBr$
$(CH_3(CH_2)_{15})P(C_4H_9)_3Br$

Preferred of these are the first two listed.

The promoter may be a quaternary ammonium halide $R''NR_3X$ typified by the following:

TABLE IV $(C_6H_5CH_2)N(C_2H_5)_3Cl$
$(CH_3)_4NBr$
$CH_3(CH_2)_{17}(C_6H_5CH_2)N(CH_3)_2Cl$
$(CH_3(CH_2)_{15}(C_6H_5CH_2)N(CH_3)_2Cl$
$(CH_3(CH_2)_{15})N(C_4H_9)_3Br$

The first listed is preferred.

It is a thus feature of the method of this invention that the catalyst may be

and the promoter may be MX, BX$_3$, BR'$_3$, B(OR')$_3$, R'R$_3$PX, or R'NR$_3$X. Illustrative of specific catalyst systems may be the following:

TABLE V

| Catalyst | Promoter |
|---|---|
| Cu(OMe)Cl | LiCl |
| Cu(OMe)Cl | MgCl$_2$ |
| Cu(OMe)Cl | KCl |
| Cu(OMe)Cl | CaCl$_2$ |
| Cu(OMe)Cl | BF$_3$ |
| Cu(OMe)Cl | (C$_6$H$_5$CH$_2$)P(C$_6$H$_5$)$_3$Cl |
| Cu(OME)Cl | (C$_4$H$_9$)$_4$PBr |
| Cu(OMe)Cl | (Me)$_4$NBr |
| Cu(OMe)Cl | (C$_6$H$_5$CH$_2$)N(C$_2$H$_5$)$_3$Cl |

It may be possible to prepare the catalyst system in situ. For example, in one embodiment, there may be added to the reaction mixture, CuCl$_2$ and Mg(OMe)$_2$ which react to give the catalyst system including Cu(OMe)Cl catalyst and MgCl$_2$ promoter.

Although Cu(II) compounds appear to be preferred, it may be possible to utilize systems containing Cu(I) typified by Cu$_2$Cl$_2$ plus Cu(OMe)Cl or Cu(OCH$_3$)$_2$; i.e. systems in which the functioning catalyst system may be a mixed-valent Cu(I and II).

The preferred catalyst system may be those containing Cu(OMe)Cl and (C$_6$H$_5$CH$_2$)N(C$_2$H$_5$)$_3$Cl; Cu(OMe)Cl and MgCl$_2$ or CaCl$_2$; Cu(OMe)Cl and BF$_3$; and Cu(OMe)Cl, (C$_6$H$_5$CH$_2$)N(C$_2$H$_5$)$_3$Cl, and CaCl$_2$ or BF$_3$.

It should be noted that the promoter may be present in the catalyst system in amount of 0.01-5 moles, preferably 0.5-2 moles, say 1 mole per mole of catalyst.

The catalyst system may be present in the reaction mixture in amount of 0.01-50 parts, preferably 0.01-20 parts, say 10 parts per 100 parts of charge alcohol.

Practice of the method of this invention may be carried out by adding 100 parts of the alcohol ROH, preferably methanol to the reaction mixture. The catalyst system may then be added. The system is then subjected to inert gas typically nitrogen at a partial pressure of 5-1000 psi, preferably 100-300 psi, say 100 psi and heated to 20° C.-170° C., preferably 80°-120° C., say 90° C. at a total pressure of 10-2000 psi, preferably 150-600 psi, say 150 psi over 0.25-2 hours, say 0.5 hour.

Carbon monoxide-containing gas is then admitted to a carbon monoxide partial pressure of 5-3000 psi, preferably 100-900 psi, say 350 psi over 0.25-10 hours, say 1 hour.

During this period, the following reaction occurs in the preferred embodiment:

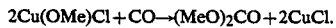

2Cu(OMe)Cl+CO→(MeO)$_2$CO+2CuCl.

At the end of this time, the reaction mixture may be rapidly cooled to 20° C.-90° C., say 25° C. at total pressure of 15-3000 psi, say 350 psi.

The reaction mixture may be distilled to azeotropically distill off product typically dimethyl carbonate and methanol. This product may be withdrawn as is or further treated to effect greater purification of the dimethyl carbonate.

The residual catalyst system (0.1-50 parts, say 10 parts) may be regenerated as by contacting with oxygen-containing gas, typically air at 20° C.-65° C., say 45° C. for 1-50 hours, say 6 hours in the presence of excess alcohol-typically methanol in amounts of 100 parts.

During this regeneration step, the following reaction occurs in the preferred embodiment:

2CuCl + 2MeOH + ½O$_2$ ⟶ 2Cu(OMe)Cl + H$_2$O

At the end of the regeneration period the catalyst in methanol may be recycled if the water content is less than about 5 wt.%. If more water than this is present, the catalyst may be separated and then dried by heating to 30° C.-60° C., say 40° C. (under reduced pressure) for 1-10 hours, say 6 hours to yield a substantially anhydrous catalyst system which is recycled using anhydrous methanol.

Product, typically dimethyl carbonate, is recovered in yield (which varies depending on the catayst system) of 60% or more; and with the preferred catalyst systems, yields of 95%-100% may be attained. Dimethyl carbonate may be used as a solvent, a gasoline extender and octane enhancer and as a reactant in place of phosgene in the preparation of isocyanates, polycarbonates, and various agricultural and pharmaceutical intermediates.

Practice of the method of this invention will be apparent to those skilled in the art from the following wherein as elsewhere in this specification, all parts are parts by weight unless otherwise noted.

DESCRIPTION OF PREFERRED EMBODIMENTS

Example I

In this example which represents the best mode known of practicing the method of this invention, there is added to the reaction vessel 190 ml of anhydrous methanol and 18.2 g (0.14 mol) of anhydrous Cu(OMe)Cl and 16 g of anhydrous benzyltriethylammonium chloride promoter (C$_6$H$_5$CH$_2$)N(C$_2$H$_5$)$_3$Cl.

The reaction mixture is pressurized to 100 psig with nitrogen, heated to 90° C. and maintained at 90° C. for 0.5 hour. The pressure is increased to 500 psig with carbon monoxide and stirring is continued for 0.5 hour. The reaction mixture is then cooled to room temperature, and depressurized. The reaction mixture is distilled with added methanol (200 ml) to recover azeotrope containing methanol and dimethyl carbonate. Analysis by Gas Chromatography indicates a yield (based on copper salt) of 101%.

Yield of dimethyl carbonate is determined (by gas chromotographic analyses using 3-pentanone as internal standard) based on copper salt added and 100% dimethyl carbonate selectivity.

Methanol is added (100 ml) and the catalyst is regenerated by bubbling air through the suspension at 45° C. for 6 hours.

In each of Examples II-X, the conditions of Example I are followed except that the promoter is different.

In Example II, no promoter is present. In Examples II, and IV-VII, after the initial run, the catalyst is regenerated by contact with air for 6 hours at 45° C. in the presence of excess methanol. In each case, the catalyst is Cu(OMe)Cl 18.2 g (0.14 mol). (Numbers in parentheses represent the yield which is attained in a subsequent run in which the catalyst used has been regenerated, the reaction conditions being otherwise the same).

TABLE VI

| Example | Promoter | Moles | % Yield |
|---|---|---|---|
| II | — | | 19 (22) |
| III | $PdCl_2$ | 0.0014 | 22 |
| IV | KCl | 0.07 | 17 (28) |
| V | $CaCl_2$ | 0.07 | 58 (67) |
| VI | $CaCl_2$ | 0.0175 | 29 (47) |
| VII | $BF_3.Et_2O$ | 0.07 | 51 (64) |
| VIII | $C_6H_5CH_2P(C_6H_5)_3Cl$ | 0.07 | 59 |
| IX | $(C_4H_9)_4PBr$ | 0.07 | 69 |
| X | $(CH_3)_4NBr$ | 0.07 | 64 |

A further series of runs was carried out in excess methanol at 90° C. and 400 psig CO (initial pressure at 20° C.) for 50 minutes using Cu(OMe)Cl as catalyst 37 g (0.285 mol):

TABLE VII

| Example | Promoter | Moles | % Yield |
|---|---|---|---|
| XI | — | | 25 |
| XII | LiCl | 0.14 | 72 |
| XIII | $MgCl_2$ | 0.14 | 79 |
| XIV | KCl | 0.14 | 92 |
| XV | $CaCl_2$ | 0.14 | 95 |

It will be noted (cf Example IV and XIV) that when potassium chloride is employed, the yield may be increased from 17% up to 92% by increasing the time of reaction from 30 minutes (Example IV) to 50 minutes (Example XIV). It should be noted that the reaction conditions for these two examples are different (Example IV: 500 psig with 70%CO–30%$N_2$, measured at 90° C. and Example XIV: 400 psig with 100% CO, measured at 20° C.)

Another series of runs was carried out in excess methanol at 400 psig CO (initial pressure at 20° C.) and 90° C. for 4 hours.

TABLE VIII

| Example | Copper Salt | Moles | Promoter | Moles | % Yield |
|---|---|---|---|---|---|
| XV | — | — | $Mg(OMe)_2$ | | 0 |
| XVII | $CuCl_2$ | 0.2 | $Mg(OMe)_2$ | 0.2 | 60 |
| XVIII | $CuCl_2$ | 0.4 | $Mg(OMe)_2$ | 0.2 | 93 |
| XIX | Cu(OMe)Cl | 0.28 | — | | 76 |
| XX | Cu(OMe)Cl | 0.28 | $MgCl_2$ | 0.14 | 99 |

From the above Tables, the following conclusions may be noted inter alia:

(i) Highest yields of dimethyl carbonate are obtained when the catalyst is Cu(OMe)Cl and the promoter is benzyltriethylammonium chloride (Ex. I) or $MgCl_2$ (Ex. XX) or $CaCl_2$ (Ex. XV).

(ii) Good yields may be attained with the catalyst systems of this invention.

(iii) High yields may be attained when the catalyst system is generated in situ (Ex. XVIII) from $CuCl_2$ and $Mg(OMe)_2$.

(iv) Generally the use of regenerated catalyst (Ex. II and IV–VII) gives yields which are improved by a substantial factor over the use of the same catalyst in the initial run.

(v) A comparison of Examples XIX and XX indicates that the yield may be increased substantially (99%/76% or 1.3 times) by use of the system of this invention.

(vi) Comparison of Examples XVII and XVIII shows that use of increased quantities of $CuCl_2$ gives increased yields.

It will be apparent to those skilled in the art that the process of this invention makes it possible to obtain higher yields of dimethyl carbonate in shorter times i.e. to increase the rate of formation of desired dimethyl carbonate. Thus in Example XX, it is shown to be possible to attain 99% yield in 4 hours using $MgCl_2$ as promoter. Example XIII shows that it is possible to attain 79% yield after 50 minutes.

If $CaCl_2$ is used as promoter (Example XV), a yield of 95% is attained after 50 minutes. Thus $CaCl_2$ is preferred (on a basis of yield in given time) to $MgCl_2$.

Generally it is possible to attain higher yield by running the reaction for a longer time or by using regenerated and recycled catalyst.

In a further series of runs, the procedure of Example I is duplicated (except that the time of reaction is only 15 minutes) with different promoters:

TABLE IX

| Example | Promoter | Moles | % Yield |
|---|---|---|---|
| XXI | $(C_6H_5CH_2)N(C_2H_5)_3Cl$ | 0.07 | 14 |
| XXII | $BF_3$ plus | 0.035 | |
| | $(C_6H_5CH_2)N(C_2H_5)_3Cl$ | 0.035 | 71 |
| | 1:1 mole ratio | | |
| XXIII | $CaCl_2$ plus | 0.035 | 68 |
| | $(C_6H_5CH_2)N(C_2H_5)_3Cl$ | 0.035 | |
| | 1:1 mole ratio | | |

Although this invention has been illustrated by reference to specific embodiments, it will be apparent to those skilled in the art that various changes and modifications may be made which clearly fall within the scope of this invention.

What is claimed is:

1. A composition of matter comprising
   (a) a copper hydrocarbonoxy halide Cu(OR')X wherein R' is a hydrocarbon group selected from the group consisting of alkyl, alkaryl, aralkyl, cycloalkyl, and aryl and X is halide; and
   (b) at least one second component selected from the group consisting of $BX_3$, $BR'_3$, $B(OR')_3$, $R'R_3PX$, and $R'R_3NX$ wherein R is selected from the same group as R'.

2. A composition of matter as claimed in claim 1 wherein R' is $C_1-C_{10}$ alkyl.

3. A composition of matter as claimed in claim 1 wherein R' is methyl.

4. A composition of matter as claimed in claim 1 wherein X is chloride.

5. A composition of matter as claimed in claim 1 wherein Cu(OR')X is copper methoxy chloride.

6. A composition of matter as claimed in claim 1 wherein $BX_3$ is $BF_3$.

7. A composition of matter as claimed in claim 1 wherein $BR_3$ is triphenyl boron.

8. A composition of matter as claimed in claim 1 wherein $B(OR')_3$ is methyl borate $B(OMe)_3$.

9. A composition of matter as claimed in claim 1 wherein $R'R_3PX$ is $(C_6H_5CH_2)P(C_6H_5)_3Cl$ or $(C_4H_9)_4P\ Br$ 10. A composition of matter as claimed in claim 1 wherein $R'R_3NX$ is $(C_6H_5CH_2)N(C_2H_5)_3Cl$ 11. A composition of matter comprising copper methoxy chloride Cu(OMe)Cl and benzyl triethylammonium chloride $(C_6H_5CH_2)N(C_2H_5)_3Cl$

* * * * *